United States Patent
Chen et al.

(10) Patent No.: US 7,817,839 B2
(45) Date of Patent: Oct. 19, 2010

(54) SYSTEM AND METHOD FOR ADAPTIVE SPATIAL COMPOUNDING FOR ULTRASOUND IMAGING

(75) Inventors: Yunqiang Chen, Plainsboro, NJ (US); Jason Jenn-Kwei Tyan, Princeton, NJ (US)

(73) Assignee: Siemens Corporation, Iselin, NJ (US)

( * ) Notice: Subject to any disclaimer, the term of this patent is extended or adjusted under 35 U.S.C. 154(b) by 937 days.

(21) Appl. No.: 11/566,328

(22) Filed: Dec. 4, 2006

(65) Prior Publication Data
US 2007/0232914 A1    Oct. 4, 2007

Related U.S. Application Data

(60) Provisional application No. 60/742,967, filed on Dec. 7, 2005.

(51) Int. Cl.
*G06K 9/00* (2006.01)
(52) U.S. Cl. .................................... 382/132; 382/260
(58) Field of Classification Search ................ 382/260, 382/128, 131, 132; 359/559; 600/437
See application file for complete search history.

(56) References Cited

U.S. PATENT DOCUMENTS

2005/0053305 A1*  3/2005  Li et al. ................... 382/260
2007/0083114 A1*  4/2007  Yang et al. ............... 600/437

\* cited by examiner

*Primary Examiner*—Vu Le
*Assistant Examiner*—Claire Wang

(57) ABSTRACT

A method for removing speckle noise from ultrasound images includes providing a plurality of digitized ultrasound (US) images, each image comprising a plurality of intensities corresponding to a domain of points on a 2-dimensional grid, initializing an initial gain associated with each of said plurality of US images, estimating a signal sub-space by averaging over each US image divided by its associated gain, and estimating an updated gain by projecting its associated image into said signal sub-space. If an absolute difference of said updated gain and said initial gain is less than a pre-determined quantity, obtaining an averaged image from said signal sub-space, estimating an optimal Wiener filter from said plurality of US images and said averaged image, and filtering said averaged image with said Wiener filter, wherein said speckle noise is substantially minimized.

20 Claims, 3 Drawing Sheets

(a) Simple averaging of multiple images     (b) Adaptive compounding result

Adaptive Spatial Compounding

11

M images

SYSTEM AND METHOD FOR ADAPTIVE SPATIAL COMPOUNDING FOR ULTRASOUND IMAGING

CROSS REFERENCE TO RELATED UNITED STATES APPLICATIONS

This application claims priority from: "Adaptive Spatial Compounding for Ultrasound Imaging", U.S. Provisional Application No. 60/742,967 of Chen, et al., filed Dec. 7, 2005, the contents of which are incorporated herein by reference.

TECHNICAL FIELD

This invention is directed to the processing of ultrasound images.

DISCUSSION OF THE RELATED ART

Ultrasonography uses high-frequency sound waves, which are transmitted from a probe into an anatomical structure. As the sound waves strike internal structures, they are reflected back to the probe and converted into an electric signal. The signal is subsequently reconstructed as an image on a monitor, which can be used to make a dynamic evaluation of the structure or can be photographed to document pathology.

Sound is emitted in a parallel, longitudinal wave pattern, similar to that of light. The frequency of the sound wave is the number of cycles, or oscillations, per second measured in hertz (Hz). For sound to be considered ultrasound, it must have a frequency of greater than 20,000 oscillations per second, or 20 KHz, rendering it inaudible to human ears. The higher the frequency of the ultrasound, the shorter the wavelength (distance from the peak of one wave to the peak of the next wave). A direct relationship exists between wavelength and depth of tissue penetration (the shorter the wavelength, the more shallow the penetration). However, as the wavelength shortens, the image resolution improves. The frequencies of ultrasound required for medical imaging are in the range 1-20 MHz.

The velocity of the sound wave is dependent on the density of the medium through which the sound travels. Sound travels faster through solids than liquids, an important principle to understand since the living tissue is composed of both. The speed also depends on temperature, pressure and other factors. Typical speeds are approximately 330 m/s in air, 1500 m/s in water and 5000 m/s in a metal.

When sound travels from one medium to another medium of different density, part of the sound is reflected from the interface between those media back into the probe. This is known as an echo; the greater the density difference at that interface, the stronger the echo, or the higher the reflectivity.

Each layer of tissue in the body produces a separate reflection of the ultrasound signal, which shows up as a peak on a trace. This gives rise to the name of one ultrasound technique, an amplitude-scan or A-scan. A-scan ultrasound biometry, commonly referred to as an A-scan, is routine type of diagnostic test used in ophthalmology that provides data on the shape of the eye. In A-scan ultrasonography, a thin, parallel sound beam is emitted, which passes through the structure and images one small axis of tissue, the echoes of which are represented as spikes arising from a baseline. The stronger the echo, the higher the spike. The amplitude of the peaks depends on the difference in acoustic impedance between the tissues on each side of each boundary. It also depends on how much of the sound is absorbed as it travels through each layer, an effect which complicates the interpretation of the scan. For example, in the eye, the vitreous is less dense than the vitreous hyaloid, which, in turn, is much less dense than the retina. Therefore, the spike obtained as sound strikes the interface of the vitreous and hyaloid is shorter than the spike obtained when the sound strikes the hyaloid-retinal interface.

B-scan ultrasonography, or B-scan, is another diagnostic test used in ophthalmology to produce a two-dimensional, cross-sectional view of the eye and the orbit. In B-scan ultrasonography, the amplitude of each returning signal is not simply displayed on a graph or oscilloscope screen. An oscillating sound beam is emitted, which passes through a structure and images a slice of tissue, the echoes of which are represented as a multitude of dots that together form an image on the screen. The stronger the echo, the brighter the dot. The amplitude controls the brightness of the spot which represents this reflection, the b for brightness giving rise to the name B-scan. So a single pulse of ultrasound passing into a series of tissues will give rise to a series of spots, with the brightness of the spots corresponding to the amplitude of the reflection from different layers. Using the eye example, the dots that form the posterior vitreous hyaloid membrane are not as bright as the dots that form the retinal membrane. This can be useful in differentiating a benign condition, such as posterior vitreous detachment, from a blinding condition, such as a more highly reflective retinal detachment. B-scan ultrasound is most useful when direct visualization of internal structures is difficult or impossible.

Ultrasound B-Scans are affected by multiplicative speckle noise, which is a random, deterministic, interference pattern formed by coherent radiation of sub-resolution scatterers. The texture of the observed speckle pattern does not correspond to the underlying structure and has a negative impact on ultrasonic images by reducing the contrast, lowering the signal to noise ratio (SNR) and obscuring important diagnostic details.

Different compounding techniques have been proposed to exploit a series of input images obtained at different conditions, such as shifted position or different ultrasound frequencies, to produce a single, improved output image. Although various algorithms have been proposed to implement these compounding techniques, they have not proven successful because of simplified assumptions on the image formation process and failure to fully utilize the abundant information hinted at by the multiple images.

Many filtering techniques, such as the Wiener Filter, have been developed to reduce the noise based on the spatial correlations of the noise and signal. One issue concerns obtaining accurate estimation of the power spectrums of the noise and signals, especially when the signal is spatial variant. Some adaptive techniques can operate on a single image, however, with multiple images, one should be able to obtain a more accurate estimation of the signal and noise properties than using a technique solely based on an averaged image.

SUMMARY OF THE INVENTION

Exemplary embodiments of the invention as described herein generally include methods and systems for spatial compounding that fully utilizes multiple images that can be easily extended to other compounding methods such as frequency compounding. Improved compounding results are obtained using a more realistic image formation model that allows different gain in different images so that multiple transducers can be used in spatial compounding. A recursive algorithm automatically estimates the gain and optimal weight of the different images for reducing the noise. Information provided by the multiple images is exploited to estimate the spatial variant properties, such as power spectrum of the signal and noise. An optimal filter can be designed to significantly reduce the noise further.

According to an aspect of the invention, there is provided a method for removing speckle noise from ultrasound images, including the steps of providing a plurality of digitized ultrasound (US) images, each image comprising a plurality of intensities corresponding to a domain of points on a 2-dimensional grid, initializing an initial gain associated with each of said plurality of US images, estimating a signal sub-space by averaging over each US image divided by its associated gain, estimating an updated gain by projecting its associated image into said signal sub-space, wherein if an absolute difference of said updated gain and said initial gain is less than a pre-determined quantity, obtaining an averaged image from said signal sub-space, estimating an optimal Wiener filter from said plurality of US images and said averaged image, and filtering said averaged image with said Wiener filter, wherein said speckle noise is substantially minimized.

According to a further aspect of the invention, if said absolute difference of said updated gain and said initial gain is greater than said pre-determined quantity, re-initializing said initial gain to said updated gain, and repeating said steps of estimating a signal sub-space and estimating an updated gain.

According to a further aspect of the invention, the initial gains are initialized to 1.

According to a further aspect of the invention, the signal sub-space $\overline{S}$ is estimated from $$\overline{S} = \frac{1}{M} \sum_{i=1}^{M} \frac{w_i I_i}{\hat{g}_i^{(k)}},$$

wherein $I_i$ is an US image, $\hat{g}_i^{(k)}$ is the associated gain, where k is an iteration counter, $w_i$ is a weighting factor, and M is the number of images.

According to a further aspect of the invention, the noise in the plurality of images is independent, wherein each of the weighting factors is 1.

According to a further aspect of the invention, the updated gain $\hat{g}_i^{(k+)}$ is estimated from $$\hat{g}_i^{(k+1)} = \frac{\langle I_i, \overline{S} \rangle}{\langle \overline{S}, \overline{S} \rangle},$$

wherein $I_i$ is the associated image, and $\overline{S}$ is the signal sub-space.

According to a further aspect of the invention, the method comprises calculating a local power spectrum for said plurality of US images by averaging a local power spectrum for each US image, and a local power spectrum of said averaged image, said local power spectra calculated at each point in said images based on a small neighborhood about each said point.

According to a further aspect of the invention, the optimal Wiener filter is calculated from said power spectra of said plurality of US images and said averaged image, wherein said optimal Wiener filter is a function of point locations, and applying said optimal Wiener filter to said averaged image.

According to a further aspect of the invention, the optimal Wiener filter $H^o(d)$ is calculated from an expression equivalent to $$H^o(d) = \frac{\sqrt{M} \cdot P_{\overline{S}}(d) - P_I(d)}{(\sqrt{M} - 1) \cdot P_I(d)},$$

wherein d is a point location, M is the number of images, $P_{\overline{S}}(d)$ is the power spectrum of the averaged image, and $P_I(d)$ is the power spectrum of the plurality of US images.

According to another aspect of the invention, there is provided a program storage device readable by a computer, tangibly embodying a program of instructions executable by the computer to perform the method steps for removing speckle noise from ultrasound images.

DETAILED DESCRIPTION OF THE PREFERRED EMBODIMENTS

Figure 2:
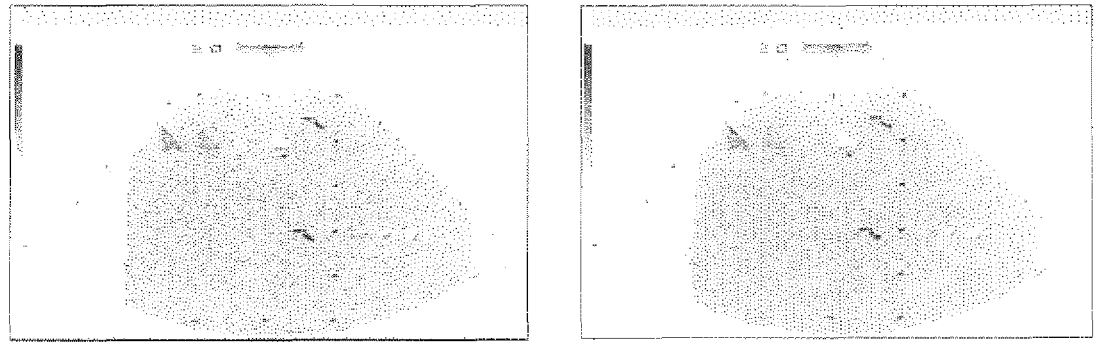
FIGS. 2(a)-(b) depicts exemplary results of adaptive spatial compounding, according to an embodiment of the invention.

Exemplary embodiments of the invention as described herein generally include systems and methods for adaptive spatial compounding in ultrasound images. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multidimensional data composed of discrete image elements (e.g. pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g. a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

In spatial compounding, several images $I_i$ of the same underlying structures are generated at different positions so that the speckle noise $N_i$ in those images is independent. In traditional compounding techniques, the multiple images are assumed to be generated by the same transducer, and hence have the same gain, and are averaged to reduce the speckle noise. In addition, some post processing on the averaged image can be applied later to further reduce the noise based on spatial dependencies. But such schemes do not fully utilize the information provided in the multiple images and are of limited usefulness in designing a good post-processing filter when the imaging device is used in different applications and a prior model of the signal and noise is hard to obtain.

If multiple transducers are used in spatial compounding, the gain $g_i$ of each transducer will be different. The speckle noise $N_i$ in the images is independent and has the same variance when the translation of the apertures of different transducers is large. But the underlying signal S is the same. Then, the following image formation model can be obtained:

$$I_i = g_i \times (S+N_i), g_i > 0,$$

where the resulting image $I_i$, the underlying signal and the noise all have spatial dependencies.

It can be easily seen that an averaging of all images is not optimal when the gains of the transducers are different. An iterative process can be used to obtain the optimal estimation of the signal and the gain of each transducer.

Figure 3:
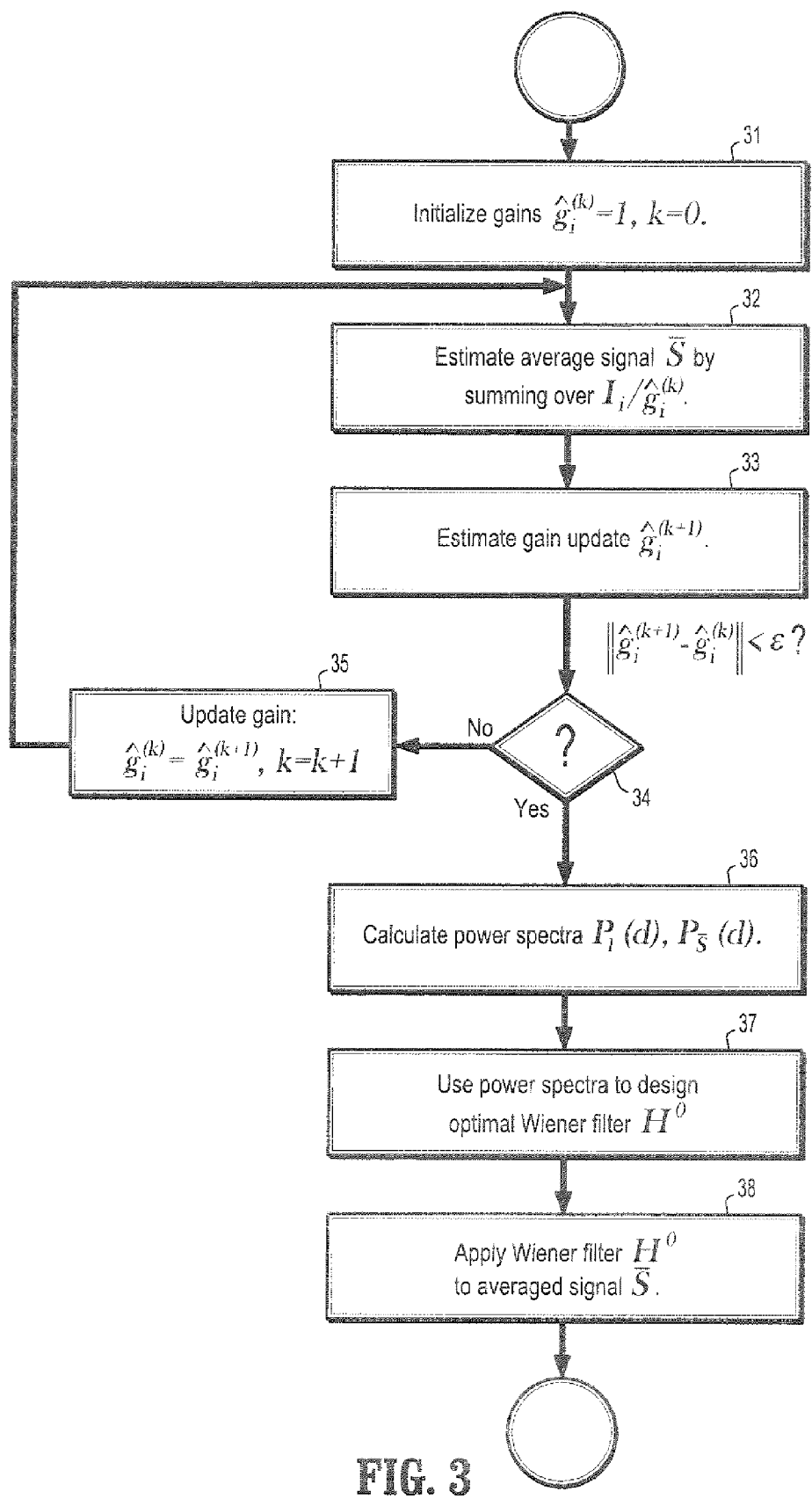
FIG. 3 is a flowchart of a method for adaptive spatial compounding, according to an embodiment of the invention.

An exemplary iterative process for estimating the signal and gain for a single transducer and image according to an embodiment of the invention is presented in FIG. 3. Referring now to the figure, the gain of each transducer is initialized at step 31 as $\hat{g}_i^{(k)}=1$, where k is an iteration counter initialized to 0. The signal sub-space can then be estimated at step 32 by summing over the images:

$$\overline{S} = \frac{1}{M} \sum_{i=1}^{M} \frac{I_i}{\hat{g}_i^{(k)}},$$

where M is the number of transducers/images. Assuming the speckle noise is independent of the signal, the gain $\hat{g}_i$, can then be estimated at step 33 by projecting the images into the signal sub-space:

$$\hat{g}_i^{(k+1)} = \frac{\langle I_i, \overline{S} \rangle}{\langle \overline{S}, \overline{S} \rangle},$$

If, at step 34, the absolute difference of the iterates is $\|\hat{g}_i^{(k+1)} - \hat{g}_i^{(k)}\| < \epsilon$, the iterative process terminates, otherwise, at step 35, the next iterate of the gain is updated as $\hat{g}_i^{(k)} = \hat{g}_i^{(k+1)}$, and the counter is updated by k=k+1. The process loops to step 32 and repeats.

This iterative procedure yields the gain $g_i$ of each input images, and the resulting averaged image $\overline{S}$ has minimal speckle noise. If the assumption that the speckle noise in the images is independent is invalid, weighting factors $w_i$ can be estimated to further adjust the weighing of each image for better noise removal:

$$\overline{S} = \frac{1}{M} \sum_{i=1}^{M} \frac{w_i I_i}{\hat{g}_i^{(k)}}.$$

An advantage of compounding is the utilization of multiple images of the same structure with independent noise. But these advantages are not fully utilized in traditional compounding techniques. Apart from reducing the noise by weighted averaging, the multiple images can also help estimate the properties of both the underlying structure and the noise so that one can better utilize the spatial dependencies in the images.

Many filtering techniques have been developed to reduce noise based on the spatial correlations of the noise and signal, such as the Wiener filter. But one of the challenges is obtaining an accurate estimation of the power spectrum of the noise and signals, especially when the signal is a spatially varying signal. With multiple images, it should be possible to obtain a more accurate estimation of the signal and noise properties than from a single averaged image.

The use of multiple images can be demonstrated with a Wiener filter, which is optimal given the power spectrum of the signal and the noise. The Wiener filter assumes that a signal and additive noise are stationary linear stochastic processes with known spectral characteristics or known autocorrelation and cross-correlation. The Wiener filter is modeled by the convolution $$x(t) = g(\tau) \circ (s(t) + n(t)),$$

where s(t) is the original signal to be estimated, n(t) is the noise, x(t) is the estimated signal which hopefully equals s(t), and $g(\tau)$ is the Wiener filter. An optimal $g(\tau)$ can be is obtained by minimizing the expectation value of the square error, $$E(e^2) = R_s(0) - 2\int_{-\infty}^{\infty} g(\tau) R_{xs}(\tau) d\tau + \int_{-\infty}^{\infty}\int_{-\infty}^{\infty} g(\tau)g[\theta] R_x(\tau - \theta) d\tau d\theta,$$

where $R_s$ is the autocorrelation function of s(t), $R_x$ is the autocorrelation function of x(t), and $R_{xs}$ is the cross-correlation function of x(t) and s(t). If the signal s(t) and the noise n(t) are uncorrelated, the cross-correlation is zero.

Figure 1:
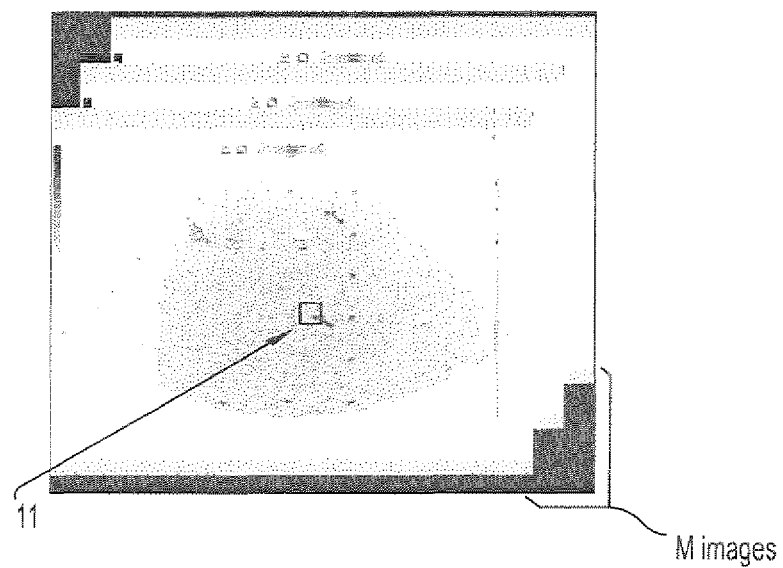
FIG. 1 illustrates the local estimation of a power spectrum in multiple images, according to an embodiment of the invention.

Using multiple images, one can estimate the power spectra of a non-stationary case, where the signal and noise spectra are constantly changing, on the fly instead of relying on some pretrained models. Referring now to FIG. 1, one can estimate the power spectra of the signal and noise at each location in an image based on a small neighborhood, such as the small square region I1 indicated in the image.

Referring again to FIG. 3, the power spectrum $P_I(d)$ around location d can be estimated at step 36 in the neighborhood of d on each image as well as the weighted averaged image, $P_{\overline{S}}(d)$. If the noise is zero-mean Gaussian distributed and independent to the signal, one obtains:

$$P_I(d) = P_S(d) + P_N(d) = \frac{1}{M}\sum_{i \in [1,M]} P_{I_i}(d) \; i=1, \ldots, M$$

$$P_{\overline{S}}(d) = P_S(d) + P_{N_i}(d)/\sqrt{M}$$

where $P_S(d)$ and $P_N(d)$ are the power spectra of the signal and noise respectively. The power spectra of both the signal and noise can be obtained for designing the optimal Wiener filter $H^0(d)$. $P_{\overline{S}}(d)$ is the power spectrum of the averaged image, which is directly estimated from the averaged image. It is the sum of the true signal power spectrum $P_S(d)$ and reduced noise power spectrum $P_N(d)/\operatorname{sqrt}(M)$, where the noise spectrum is reduced due to the averaging operation. Thus, $P_I(d)$ and $P_{\bar{S}}(d)$ can both be estimated from the images. But one needs to estimate $P_S(d)$ and $P_N(d)$ to design the Wiener filter, Based on the understanding that $P_I(d)=P_S(d)+P_N(d)$ and $P_{\bar{S}}(d)=P_S(d)+P_N(d)1\sqrt{M}$, one can estimate $P_N(d)$ and $P_S(d)$ from $P_I(d)$ and $P_{\bar{S}}(d)$ and hence design the optimal Wiener filter at step 37 as follows:

$$H^o(d) = \frac{P_S(d)}{P_S(d)+P_N(d)} = \frac{\sqrt{M}\cdot P_{\bar{S}}(d) - P_I(d)}{(\sqrt{M}-1)\cdot P_I(d)},$$

where this Wiener filter is a function of location d. The Wiener filter can be applied at step 38 to the averaged image as $H^o \times \bar{S}$ to further reduce the speckle noise.

An adaptive spatial filtering algorithm according to an embodiment of the invention was applied to compound real ultrasound images. In this experiment, 3 images were used (i.e. M=3). The weighted average will only reduce the noise level by $\sqrt{M}$. Simple averaging produces noisy results such as those shown in FIG. 2(a).

One can see from FIG. 2(a) that the noise appears more independent between the neighboring pixels than with respect to the signal. By averaging the neighborhood in the image, one should be able to reduce the noise level. But the challenge is to prevent oversmoothing across signal boundaries. However, because the power spectrum of the noise and signal can be estimated to design an optimal Wiener filter for each location, an improved filter can be used to remove the speckle noise while keeping the signal boundary sharp. The results of applying an optimal Wiener filer of an embodiment of the invention is shown in FIG. 2(b), where the reduction of noise is apparent.

Based on different imaging characteristics, alternative implementations can achieve improved compounding. According to another embodiment of the invention, if the noise is not Gaussian distributed but rather includes a heavy tail distribution, such as salt and pepper noise, higher order statistical filters, such as a weighted median filter, can be used between multiple images instead of weighted averaging. According to another embodiment of the invention, prior knowledge can be exploited in the adaptive Wiener filtering. For example, since the structures of interest are usually tissue boundaries, the signal can be modeled by a quadratic signal for improved power spectrum estimation.

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device, The application program can be uploaded to, and executed by, a machine comprising any suitable architecture.

Figure 4:
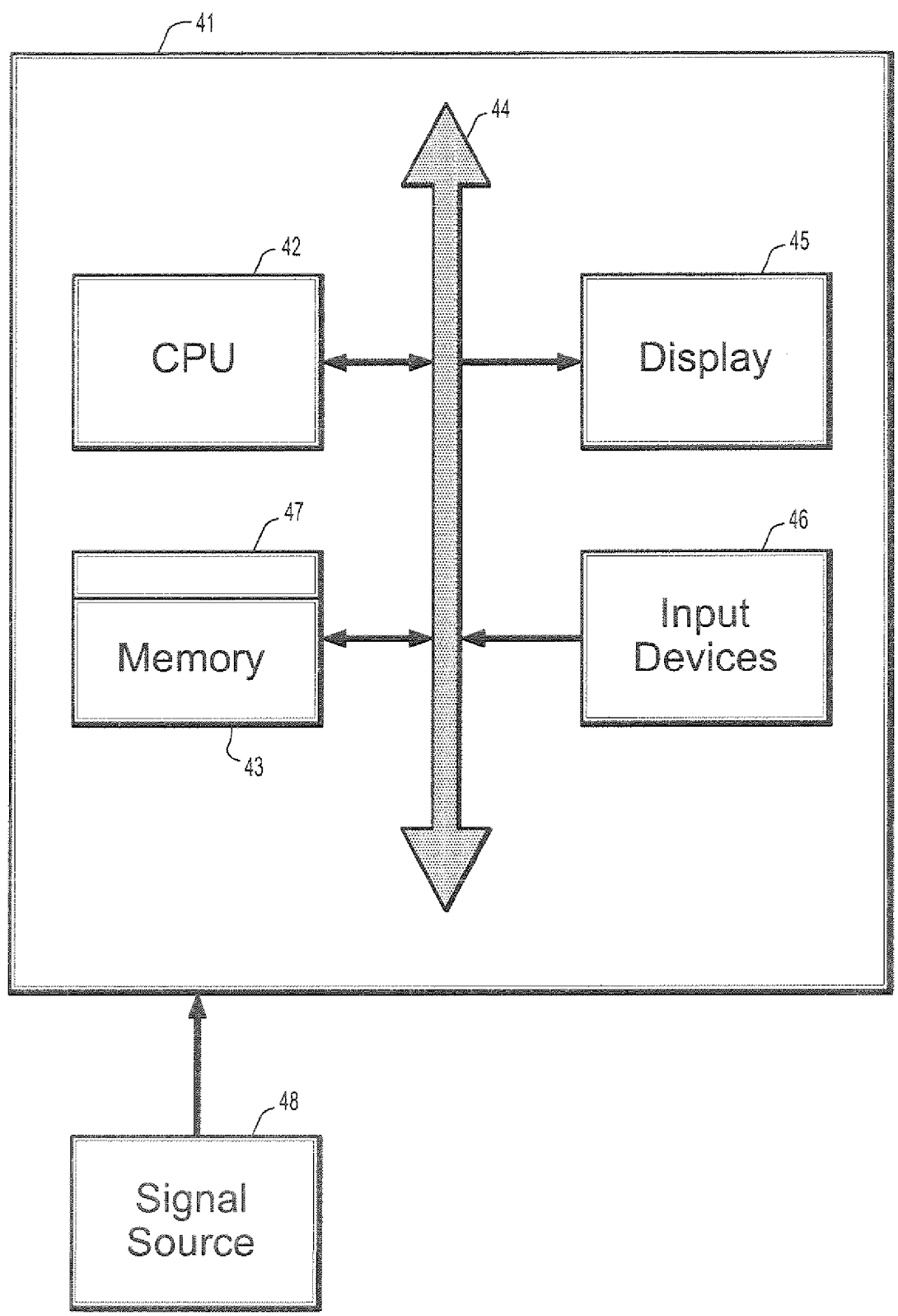
FIG. 4 is a block diagram of an exemplary computer system for implementing a method for adaptive spatial compounding, according to an embodiment of the invention.

FIG. 4 is a block diagram of an exemplary computer system for implementing a adaptive spatial filter according to an embodiment of the invention. Referring now to FIG. 4, a computer system 41 for implementing the present invention can comprise, inter alia, a central processing unit (CPU) 42, a memory 43 and an input/output (I/O) interface 44. The computer system 41 is generally coupled through the I/O interface 44 to a display 45 and various input devices 46 such as a mouse and a keyboard. The support circuits can include circuits such as cache, power supplies, clock circuits, and a communication bus. The memory 43 can include random access memory (RAM), read only memory (ROM), disk drive, tape drive, etc., or a combinations thereof. The present invention can be implemented as a routine 47 that is stored in memory 43 and executed by the CPU 42 to process the signal from the signal source 48. As such, the computer system 41 is a general purpose computer system that becomes a specific purpose computer system when executing the routine 47 of the present invention.

The computer system 41 also includes an operating system and micro instruction code. The various processes and functions described herein can either he part of the micro instruction code or part of the application program (or combination thereof which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method of removing speckle noise from ultrasound images comprising the steps of:
   providing a plurality of digitized ultrasound (US) images, each image comprising a plurality of intensities corresponding to a domain of points on a 2-dimensional grid;
   initializing an initial gain associated with each of said plurality of US images;
   estimating a signal sub-space by averaging over each US image divided by its associated gain;
   estimating an updated gain by projecting its associated image into said signal sub-space, wherein if an absolute difference of said updated gain and said initial gain is less than a pre-determined quantity, obtaining an averaged image from said signal sub-space;
   estimating an optimal Wiener filter from said plurality of US images and said averaged image; and
   filtering said averaged image with said Wiener filter, wherein said speckle noise is substantially minimized.

2. The method of claim 1 wherein if said absolute difference of said updated gain and said initial gain is greater than said pre-determined quantity, re-initializing said initial gain to said updated gain, and repeating said steps of estimating a signal sub-space and estimating an updated gain.

3. The method of claim 1, wherein said initial gains are initialized to 1.

4. The method of claim 1, wherein said signal sub-space $\bar{S}$ is estimated from $$\bar{S} = \frac{1}{M}\sum_{i=1}^{M}\frac{w_i I_i}{\hat{g}_i^{(k)}},$$

wherein $I_i$ is an US image, $\hat{g}_i^{(k)}$ is the associated gain, where k is an iteration counter, $w_i$ is a weighting factor, and M is the number of images.

5. The method of claim 4, wherein the noise in the plurality of images is independent, wherein each of the weighting factors is 1.

6. The method of claim 1, wherein the updated gain $\hat{g}_i^{(k+)}$ is estimated from $$\hat{g}_i^{(k+1)} = \frac{\langle I_i, \bar{S} \rangle}{\langle \bar{S}, \bar{S} \rangle},$$

wherein $I_i$ is the associated image, and $\bar{S}$ is the signal sub-space.

7. The method of claim 1, further comprising calculating a local power spectrum for said plurality of US images by averaging a local power spectrum for each US image, and a local power spectrum of said averaged image, said local power spectra calculated at each point in said images based on a small neighborhood about each said point.

8. The method of claim 7, wherein said optimal Wiener filter is calculated from said power spectra of said plurality of US images and said averaged image, wherein said optimal Wiener filter is a function of point locations, and applying said optimal Wiener filter to said averaged image.

9. The method of claim 8, wherein said optimal Wiener filter $H^0(d)$ is calculated from an expression equivalent to $$H^0(d) = \frac{\sqrt{M} \cdot P_{\bar{S}}(d) - P_I(d)}{(\sqrt{M} - 1) \cdot P_I(d)},$$

wherein d is a point location, M is the number of images, $P_{\bar{S}}(d)$ is the power spectrum of the averaged image, and $P_I(d)$ is the power spectrum of the plurality of US images.

10. A method of removing speckle noise from ultrasound images comprising the steps of:
providing a plurality of digitized ultrasound (US) images $I_i$, each image comprising a plurality of intensities corresponding to a domain of points on a 2-dimensional grid;
iteratively approximating a gain associated with each of said US images, whereby an averaged signal $\bar{S}$ is obtained;
calculating a local power spectrum for said plurality of US images by averaging a local power spectrum for each US image, and a local power spectrum of said averaged image, said local power spectra calculated at each point in said images based on a small neighborhood about each said point;
calculating an optimal Wiener filter $H^0(d)$ from said power spectra of said plurality of US images and said averaged image from an expression equivalent to $$H^0(d) = \frac{\sqrt{M} \cdot P_{\bar{S}}(d) - P_I(d)}{(\sqrt{M} - 1) \cdot P_I(d)},$$

wherein d is a point location, M is the number of images, $P_{\bar{S}}(d)$ is the power spectrum of the averaged image, and $P_I(d)$ is the power spectrum of the plurality of US images, and applying said optimal Wiener filter to said averaged image $\bar{S}$ wherein said speckle noise is substantially minimized.

11. The method of claim 10, wherein iteratively approximating said gain comprises initializing an initial gain associated with each of said plurality of US images;
estimating a signal sub-space by averaging over each US image divided by its associated gain; and
estimating an updated gain by projecting its associated image into said signal sub-space, wherein said steps of estimating a signal sub-space and estimating an updated gain are repeated until an absolute difference of said updated gain and said initial gain is less than a pre-determined quantity.

12. A non-transitory program storage device readable by a computer, tangibly embodying a program of instructions executable by the computer to perform the method steps for removing speckle noise from ultrasound images, said method comprising the steps of:
providing a plurality of digitized ultrasound (US) images, each image comprising a plurality of intensities corresponding to a domain of points on a 2-dimensional grid;
initializing an initial gain associated with each of said plurality of US images;
estimating a signal sub-space by averaging over each US image divided by its associated gain;
estimating an updated gain by projecting its associated image into said signal sub-space, wherein if an absolute difference of said updated gain and said initial gain is less than a pre-determined quantity, obtaining an averaged image from said signal sub-space;
estimating an optimal Wiener filter from said plurality of US images and said averaged image; and
filtering said averaged image with said Wiener filter, wherein said speckle noise is substantially minimized.

13. The computer readable program storage device of claim 12, wherein if said absolute difference of said updated gain and said initial gain is greater than said pre-determined quantity, re-initializing said initial gain to said updated gain, and repeating said steps of estimating a signal sub-space and estimating an updated gain.

14. The computer readable program storage device of claim 12, wherein said initial gains are initialized to 1.

15. The computer readable program storage device of claim 13, wherein said signal sub-space $\bar{S}$ is estimated from $$\bar{S} = \frac{1}{M} \sum_{i=1}^{M} \frac{w_i I_i}{\hat{g}_i^{(k)}},$$

wherein $I_i$ is an US image, $\hat{g}_i^{(k)}$ is the associated gain, where k is an iteration counter, $w_i$ is a weighting factor, and M is the number of images.

16. The computer readable program storage device of claim 15, wherein the noise in the plurality of images is independent, wherein each of the weighting factors is 1.

17. The computer readable program storage device of claim 13, wherein the updated gain $\hat{g}_i^{(k+)}$ is estimated from $$\hat{g}_i^{(k+1)} = \frac{\langle I_i, \bar{S} \rangle}{\langle \bar{S}, \bar{S} \rangle},$$

wherein $I_i$ is the associated image, and $\bar{S}$ is the signal sub-space.

18. The computer readable program storage device of claim 12, the method further comprising calculating a local power spectrum for said plurality of US images by averaging a local power spectrum for each US image, and a local power spectrum of said averaged image, said local power spectra calculated at each point in said images based on a small neighborhood about each said point.

19. The computer readable program storage device of claim 18, wherein said optimal Wiener filter is calculated from said power spectra of said plurality of US images and said averaged image, wherein said optimal Wiener filter is a function of point locations, and applying said optimal Wiener filter to said averaged image.

20. The computer readable program storage device of claim 19, wherein said optimal Wiener filter $H^0(d)$ is calculated from an expression equivalent to $$H^0(d) = \frac{\sqrt{M} \cdot P_{\bar{S}}(d) - P_I(d)}{(\sqrt{M} - 1) \cdot P_I(d)},$$

wherein d is a point location, M is the number of images, $P_{\bar{S}}(d)$ is the power spectrum of the averaged image, and $P_I(d)$ is the power spectrum of the plurality of US images.

* * * * *